(12) United States Patent
Slade

(10) Patent No.: US 10,471,169 B2
(45) Date of Patent: Nov. 12, 2019

(54) VOLATILE MATERIAL DISPENSER, AND DISPENSING SCREEN THEREOF

(75) Inventor: Brian Parry Slade, Kent (GB)

(73) Assignee: I&I DEVELOPMENTS LTD., Surrey (GB)

( * ) Notice: Subject to any disclaimer, the term of this patent is extended or adjusted under 35 U.S.C. 154(b) by 0 days.

(21) Appl. No.: 13/821,891

(22) PCT Filed: Sep. 12, 2011

(86) PCT No.: PCT/GB2011/001337
§ 371 (c)(1),
(2), (4) Date: Sep. 17, 2013

(87) PCT Pub. No.: WO2012/032310
PCT Pub. Date: Mar. 15, 2012

(65) Prior Publication Data
US 2014/0001281 A1    Jan. 2, 2014

(30) Foreign Application Priority Data
Sep. 10, 2010  (GB) .................................. 1015168.6

(51) Int. Cl.
*A61L 9/12* (2006.01)
*A01M 1/20* (2006.01)

(52) U.S. Cl.
CPC .......... *A61L 9/127* (2013.01); *A01M 1/2044* (2013.01); *A61L 2209/135* (2013.01)

(58) Field of Classification Search
CPC ................. A61L 2209/131; A61L 9/03; A61L 2209/134; A61L 2/18; A61L 9/127;
(Continued)

(56) References Cited

U.S. PATENT DOCUMENTS 1,422,059 A * 7/1922 Howard .................... F23D 3/18
                                                    431/315
4,293,095 A * 10/1981 Hamilton et al. .............. 239/35
(Continued)

FOREIGN PATENT DOCUMENTS

CN    1142192    2/1997
CN    1306446    8/2001
(Continued)

OTHER PUBLICATIONS

International Search Report for PCT/GB2011/001337 dated Dec. 2, 2011.
(Continued)

*Primary Examiner* — Viet Le
*Assistant Examiner* — Juan C Barrera
(74) *Attorney, Agent, or Firm* — Andrus Intellectual Property Law, LLP

(57) ABSTRACT

A dispensing screen for dispensing, by evaporation, volatile materials applied thereto, is provided. The screen comprises a sheet of material and diverting means formed in the plane of the sheet. The diverting means form a minimum path length along the length of the sheet between at least a portion of a first edge and an opposing second edge of the sheet, which minimum path length is longer than the distance between the first and second edges along the surface of the sheet. A dispensing apparatus is also provided, which in embodiments includes the dispensing screen of the invention, and in embodiments includes a sink for capturing un-evaporated volatile material.

27 Claims, 9 Drawing Sheets

(58) Field of Classification Search
CPC ... A61L 2209/135; A61L 9/037; B65D 75/48;
A01M 1/2044; A01M 1/2055
USPC .................................................. 239/34–60
See application file for complete search history.

(56) References Cited

U.S. PATENT DOCUMENTS

| | | | |
|---|---|---|---|
| 5,238,187 A | | 8/1993 | Zlotnik et al. |
| 2005/0001337 A1* | | 1/2005 | Pankhurst ............... A61L 9/02 261/104 |
| 2005/0189434 A1* | | 9/2005 | Burgeson ...................... 239/44 |
| 2005/0284953 A1* | | 12/2005 | Martens, III ........ A01M 1/2044 239/44 |
| 2006/0076429 A1 | | 4/2006 | Kvietok |
| 2006/0231641 A1 | | 10/2006 | Uchiyama |
| 2007/0057086 A1* | | 3/2007 | Van Kippersluis ............. 239/43 |
| 2007/0125874 A1* | | 6/2007 | Alexander ..................... 239/44 |
| 2007/0157817 A1 | | 7/2007 | Lee |

FOREIGN PATENT DOCUMENTS

| | | |
|---|---|---|
| CN | 101001648 | 7/2007 |
| EP | 0078114 | 5/1983 |
| GB | 1454040 A | 10/1976 |
| JP | 63309272 | 6/1987 |
| WO | 2000030692 | 6/2000 |
| WO | 2005021052 | 3/2005 |
| WO | 2008072109 | 6/2008 |
| WO | 2011128604 A1 | 10/2011 |
| WO | 2012033526 A | 3/2012 |

OTHER PUBLICATIONS

Search Report for GB1015168.6 dated Dec. 24, 2010.
Search Report for GB1015168.6 dated Jan. 27, 2011.
International Preliminary Report on Patentability for PCT/GB2011/001337 dated Mar. 12, 2013.
Office Action for CN2011800543568 dated Jul. 11, 2014.
Office Action for JP2013-527678 dated Aug. 4, 2015.
Canadian Office Action for Canadian Patent Application No. 2,810,957 dated Mar. 6, 2017.
Office Action for Indonesian Patent Application No. W00201301480 dated Mar. 19, 2018.
European Search Report for European Patent Application No. 17208178 dated May 16, 2018.
Office Action for RU2013115880 dated Oct. 20, 2015.

* cited by examiner

VOLATILE MATERIAL DISPENSER, AND DISPENSING SCREEN THEREOF

CROSS REFERENCE TO RELATED APPLICATION

The present application is the U.S. national stage application of International Application PCT/GB2011/001337, filed Sep. 12, 2011, which international application was published on Mar. 15, 2012, as International Publication WO2012/032310, The International Application claims priority of British Patent Application No. 1015168.6, filed Sep. 10, 2010, the contents of which are incorporated herein by reference in their entireties.

FIELD OF THE INVENTION

The present invention relates to a dispenser for dispensing volatile materials, in particular, but not limited to, fragrances, insecticides, insect repellents, anti-viral/bacterial, decongestant inhalant, pheromone and attractant materials.

BACKGROUND OF THE INVENTION

Different types of fragrance dispensers are known. Some consist of a piece of material which is impregnated with volatile scent chemicals. However, although such products initially provide high levels of scent delivery, this reduces as the concentration of scent chemicals in the material reduces. Similar disadvantages exist with gel based air fresheners, in which the fragrance material is provided in a gel and evaporates into the air.

In order to overcome such problems, dispensers in which the volatile material is stored in a reservoir and delivered to a dispensing material are known. In particular, so called "plug in" dispensers are available, in which the volatile material is dispensed with the aid of a heated wick to encourage evaporation.

Also, a wick can be used to dispense the fragrance from a reservoir. However, as fragrances generally comprise different "notes", which evaporate at different rates ("high" notes evaporating more quickly than "bottom" notes), such wicks generally become saturated and clogged with the least volatile "bottom notes" of the fragrance and the carrier material, so that their effectiveness is therefore reduced over time. A fragrance may contain several fragrance components, solvents and residues. The various components provide the character or profile of the fragrance and they have different volatilities ranging from top note (high) to bottom/end notes (low). Historically perfumers have used bottom notes to sustain conventional fragrance products over time because the volatile top notes tend not to last.

SUMMARY OF THE INVENTION

The present invention seeks to overcome or ameliorate at least one of the disadvantages of the prior art.

An aspect of the invention provides a dispensing screen which comprises a sheet, which is preferably substantially flat, and has a convoluted path formed between an application end at which a volatile material, in general in a liquid carrier, is applied, and an opposite end, towards which the volatile material flows in the liquid carrier by capillary action, gravity or a combination of both, evaporating as it flows. The convoluted path controls the rate at which the material flows along the sheet. In embodiments where gravity is used to propel the flow of material down the sheet, the convoluted path may reduce the apparent effect of gravity by preventing a fully vertical flow of the material down the sheet. The gravity flow removes the need for end power source to pump material. Further, application of fresh volatile material to the top of the sheet in embodiments washes any residue from previously applied material down the sheet to reduce clogging and the consequent reduction in performance. The sheet is effectively irrigated by newly applied carrier liquid and volatile material to "wash" down already applied material and keep the sheet clear for carrying more material for evaporation. The convoluted path increases the path length for any given size of sheet. The sheet can therefore be made more compact than would otherwise be possible, and extra structural features to support the sheet can be reduced. These factors may also serve to reduce cost of manufacture of the sheet.

Such a screen can produce constant or near-constant evaporation of the volatile material, and also consistent ratios of the different chemicals in the volatile material over time. Therefore the odour intensity, and the particular scent, do not substantially change over the lifetime of the dispenser. In the case of an insecticide, insect repellent, anti-viral/bacterial, decongestant inhalant, pheromone or attractant material use, the dispensing is constant, so the dosage of materials released is also substantially constant.

The sheet is preferably permeable. The sheet may be porous and/or woven, and/or the permeability may be due to formation of perforations, and/or by provision of holes through the sheet.

The sheet may be formed of paper or other cellulose based material. Where holes are formed, they may be circular, or may be elongated in a direction across the sheet, but in embodiments at an angle, which may be approximately 30°, to the horizontal. Such holes may provide diverting means for forming the convoluted path on the sheet. They may be formed in a herring bone, or isometric, pattern so that the extending direction of adjacent holes in the direction between the first and second edges extend in an opposite sense relative to the direction between the first and second edges. Provision of such holes exposes the material of the sheet between the two main opposing surfaces to the atmosphere, and means that volatile material being carried in the inner material of the sheet is also exposed to the atmosphere and can evaporate, which reduces the blocking of the central material of the sheet by carrier material applied to the sheet. It also increases the surface area/weight ratio for the sheet. Further, such permeability of the sheet allows multiple sheets to be placed with their main surfaces parallel to increase the total surface area for evaporation without increasing the size of sheet used, thereby keeping a dispenser in which the sheets are mounted compact. An angular, grid-like form may be provided by such holes, or by impermeable material.

In embodiments of the invention, there may be provided impermeable material on the sheet, which effectively divides the sheet into two regions. In a first region, the diverting means are formed and the volatile material is applied at one end thereof, and travels to the other end. At the other end, the two regions may be joined so that volatile material can then travel back up the other region to where the sheet is joined to a second sheet of the same or similar form and/or function as the first sheet. The volatile material can then travel down the second sheet. The second sheet may also have the two regions, or may have only one region with diverting means. This can be repeated as necessary to provide the required total path length for the volatile material. Alternatively, the sheets may all have single regions and be connected from the base of the first to the base of the second, and from the top of the second to the top of the third etc, to provide a flow path. Alternatively, multiple sheets may be mounted and fed independently. In particular, the impermeable element may extend from the first end or edge towards the second end or edge to divide the first edge and at least part of the sheet into two portions, a first portion of the sheet comprising the diverting means and a second portion of the sheet providing a direct communication channel from the region of the second edge to the second portion of the first edge to allow material that has reached the second edge to return to the second portion of the first edge.

The sheet may be formed from woven fibres, or plastics, such as polyester, or cellulose, for example. Impermeable material may be placed on the sheet to form the convoluted path. The impermeable regions may extend substantially parallel to one another, with adjacent regions extending from opposite side edges of the sheet and each providing a gap between the opposing edge and the impermeable region, the side of the material on which the gap is arranged alternating down the sheet from the first edge to the second edge. The sheet may be formed of a woven material such as a sexangular mesh fabric, with generally hexagonal tessellated spaces formed by the woven material. The hexagons may be regular or irregular; other shaped spaces than hexagonal may be formed, such as octagonal, etc. The spaces are formed so that the woven material does not run straight from one edge of the sheet to the other, but the spaces interrupt the woven material. In this way, a convoluted path between the edges of the sheet is provided.

According to a first aspect of the invention, there is provided a sheet as claimed in claim 1. Preferable features of the first aspect are provided in dependent claims.

In embodiments of the invention, the diverting means may comprise impermeable material either on the surface of or penetrating into the material of the sheet. The sheet material may comprise woven polyester fabric material. The impermeable material may be formed in a series of parallel lines forming a convoluted path from the (in use) top of the sheet to the (in use) bottom. The impermeable material may be applied to the sheet using a gel pen or the like, or may be formed from the same or similar materials to those used in a gel pen, for example water soluble biopolymers such as xanthan gum or tragacanth gum, or types of polyacrylate thickeners. Alternatively, superglue may be used. Adjacent lines may extend from alternate sides of the sheet part way across the sheet, at least half way across the sheet, to leave a gap through which the volatile material can flow. This produces the convoluted or "snaking" passage down the sheet. Again, the volatile material may flow across the sheet by one or both of capillary action and the effect of gravity. The convoluted path weakens the effect of gravity and also provides an elongated flow path to allow more time for the volatile material to evaporate from the sheet. The diverting means may comprise impermeable elements which may be formed by melting the material of the sheet. This may join fibres of the sheet together to form a solid barrier that the volatile material does not flow across, or is hindered from flowing across. The melting/softening may be achieved using a laser or a heated jig or stamp.

The sheet may be incorporated into a dispenser, for example, as disclosed in U.S. Pat. No. 6,631,891 or 7,360,671. In this case, a reservoir is provided, in which volatile material is contained. A wick extends substantially vertically down into the reservoir. The sheet may be positioned relative to the reservoir to allow siphonic feeding of the volatile material to the top of the sheet. Alternatively, the wick may be fed by the constant hydrostatic head provided by the pressure compensated reservoir disclosed in U.S. Pat. No. 7,360,671. The effective constant height of the bottom of the reservoir when using the dispenser described in these two documents provides a substantially constant flow rate of volatile material to the top of the sheet.

The material used for the sheet in the above U.S. Pat. No. 6,631,891 is a polyester fibre fabric. Polyester is known to be a stable material that is not adversely affected by many volatile materials and is commonly used for wicks to transport the fragrance by capillary action and emanate the fragrance from its outside surface. Its characteristic surface smoothness of each polyester filament made it suitable for use as a wick because of the sticky nature of the gums and residues that tend to be left behind by the fragrance. When the polyester filaments are packed together to form a wick it provides a very good means for capillary action. In spite of this, because of the nature of the fragrance material it may become progressively blocked during use. This may possibly affect its performance as a means of transport and emanation of fragrance.

The invention may use a woven polyester fabric material as an emanating screen fed from the top of the screen with fragrance to overcome the effects of progressive blocking due to the build-up of residues. Gravity and capillary forces combine to charge the fabric screen with fragrance. The principle driving the system is a siphon. The reservoir supply side of the siphon is held at a constant level while the emanating screen is the other arm of the siphon. The siphon is biased so that gravity exerts a greater force on the column of liquid residing on the fabric screen. The fragrance continuously flows down the screen at a controlled rate. The solvents in the fragrance irrigate the supply wick and the screen to prevent the build-up of residues. This maintains the performance so that the evaporation rate is linear. The bottom of the screen may be connected to a sink (e.g. absorbent granules or porous plastics) which receive the sticky residues that are washed down by bottom notes of the fragrance.

In order to get the best value out of the fragrance it is necessary to weaken the effect of gravity and increase the length of the path taken by the fragrance down the screen. This is so that the majority of the fragrance comes off of the evaporating screen rather than too much travels down into the sink. Obviously a certain amount is required to travel to the sink to keep the screen free from becoming clogged. The invention of the patent of U.S. Pat. No. 6,631,891 describes how this can be done by a method of physically bending the screen in a corrugated manner around a supporting frame. This increases the path length so that the liquid product has further to travel providing more time for the volatiles to evaporate off of the screen. The fragrance is configured into convoluted chain of molecules and the sum total of their angular disposition means that the effect of gravity is greatly reduced from what it would be if the column was vertically disposed. The two effects, weakened gravity and increased path length, combine together to slow the flow rate to maximise the evaporative capacity of the screen. However, such a bent screen increases the size of the device and requires additional manufacturing stages.

It was previously thought that polyester was the only type of material that could be used due to the smooth surface of each of the monofilaments. However the inventor has now found that other types of material, for example, absorbent papers/cards and porous plastics may also be used. The absorbent paper screens are highly permeable because most of the surface is cut away. This allows the possibility of several screens to be sited alongside each other. This provides a highly evaporative means from a relatively compact enclosure.

Dense population of the sheet with diverting means, in embodiments in the form of holes, provides a high surface area to volume ratio. Use of a 'herring bone' pattern of holes to produce convoluted pathways for the flow reduces the effect of gravity and slows the movement of the material down the sheet, so increasing the dwell time of the sheet.

The permeability of the perforated screen makes it sensitive to the movement of air, so that dispensing is increased when a person moves near the dispenser for example.

The edge of each hole is supplied with fragrance by the convoluted pathway. The cutting of the holes in the sheet surface enables fragrance to be released from the interior fibres of the paper.

The continuous evaporating means is particularly suitable for releasing insecticides as well as fragrances. Further, two or three screens may be connected in series, for example, around 3 mm apart to provide a compact system with a large surface area. However, for highly volatile materials, multiple sheets may not be necessary.

Paper (cellulose) is used in the fragrance industry for the purposes of acting as a reservoir and dispensing means. It is very basic, simple and low-cost but very inefficient in terms of constant dispensing of fragrance when it is employed in a conventional dispensing units.

Absorbent papers and porous plastic sheets have been found to work in embodiments of the present invention, when modified by the surface being perforated or having other diverting means provided to provide a convoluted path across the sheet. For example, the diverting means may comprise at least one impermeable element across which the volatile material cannot flow. The diverting means may comprise a plurality of offset parallel elements. The element (s) may be formed by melting or heat welding of the material of the sheet.

The screen can be used as a dispensing means for dispensing volatile materials, for example fragrances, insecticides, insect repellents, anti-viral/bacterial, decongestant inhalant, pheromone and attractant materials. Also by perforating the sheet materials, it is a simpler, compact and low-cost alternative to the structurally supported fabric system used in U.S. Pat. No. 6,631,891.

As described above, the main (emanating) surfaces of the sheet are provided by a dispersal sheet that is densely populated with holes in a regular herring bone pattern. The sheet may be made from absorbent paper, rigid card, fabric or a porous plastic. The thickness of the dispersal screen may vary according to which material is used, e.g. paper, card or porous plastic. The surface of the screen is heavily populated with holes cut from its surface so that the volume of the material is greatly reduced. This reduces the fragrance loading and as a result exposes more of its surface area, relative to its volume, for the purpose of evaporating the fragrance.

The result is a perforated dispersal sheet that is highly permeable so that any slight disturbance, convection currents, draughts and people traffic etc., will promote extra evaporation to waft the fragrance around.

Alternatively, use of a woven material such as a sexangular mesh fabric which provides a convoluted path between the opposing edges of the sheet, and functions in a similar way to that described above. Such a material comprises holes which form the diverting means and the convoluted path.

Capillary and gravity forces combine together to load the dispersal sheet. Gravity becomes more dominant as the capillary force diminishes as the sheet becomes loaded. Gravity acts vertically downwards on each molecule of liquid in a column, singularly and collectively. Therefore, a straight path, which was aligned vertically, makes the liquid flow down the sheet too fast to provide sufficient time for evaporation.

It can be seen that the path taken by a single molecule on the screen with a herring bone pattern/sexangular mesh fabric is convoluted. As it travels from the top to the bottom of the screen along the 'convoluted path', the distance is greater than the actual vertical length of the screen. The evaporating capacity may be directly proportional to the surface area of the or each screen.

The other effect is gravity, acting on each liquid molecule singularly and the whole column collectively. Most of the path taken by the liquid column is disposed at an angle (inclined plane) to the vertical. This slows down the effect of gravity acting on the column of liquid. The perforations in the surface of the sheet makes it highly permeable and therefore very sensitive to any small movement of surrounding air. Further, in the case of a woven material such as a sexangular mesh fabric, the tension applied to the opposing edges will affect the speed of travel of the liquid on the sheet. In particular, with higher tension, the spaces are stretched in one direction, and tend to be squashed perpendicular to that direction. Thus, the degree of convolution of the woven fibres from the opposing edges is reduced. Even if the sheet is not squashed by the applied tension in a direction perpendicular thereto, the portions of the woven material that form the sides which are neither horizontal nor vertical will be made closer to vertical, and gravity will therefore pull the volatile material down the sheet more quickly. The material can be highly permeable to air, due to the high surface area of the strands relative to the surface area of the sheet if it were solid. The strands may be fine polyester monofilaments, which may be woven into the screen. The material may be self irrigating.

It can also be seen that the convoluted path influences the fragrance material to encircle each and every hole in the surface of the emanating screen when travelling from the top of the screen towards the bottom. Capillary forces combine with gravity in helping to distribute the fragrance uniformly across the perforated screen's surface. A system employing two screens may be connected in such a way as to form a conveyor belt system for emanating the fragrance. The bottom of the first screen may be connected to the bottom of the second screen. In such an arrangement the flows on each screen would be opposite (one upwards and one downwards). The screen may be mounted in a dispensing apparatus, which may include a reservoir for storing the volatile material before it is dispensed. The screen of the apparatus may be wrapped around so that the lateral edges of the screen, extending between the first and second edges, are joined to one another along at least a portion of their length.

The dispensing screen may be mounted around the reservoir. A wick may be provided, extending from the reservoir to the dispensing screen and in fluid communication at or adjacent to the top of the dispensing screen to supply volatile material thereto.

Alternatively, the sheet may be wrapped into a cylinder. The arrangement of the sheet may otherwise be as described above. A cylindrical or other 'closed loop' design, with the cylindrical or longitudinal axis to be arranged vertically in use, allows a reservoir, which is provided to store the volatile material to be dispensed, to be placed inside the cylinder, which provides a compact and efficient design. The open nature (holes) of the screen allow the reservoir inside to be viewed.

According to a second aspect of the invention, there is provided a dispensing apparatus for dispensing volatile materials by evaporation. The apparatus may comprise a sink for catching volatile material that has not evaporated after application to dispensing means. The sink may include absorbent material to retain the volatile material. The absorbent material may be in the form of absorbent granules or porous plastic. In this way, volatile material and carrier material, again usually liquid, that is caught in the sink can be retained even if the orientation of the sink is changed. Preferably the sink is not directly touching the dispensing means, to avoid the absorbent material effectively sucking the carrier material and volatile material through the dispensing means to the sink more quickly than desired, so reducing the dwell time on the dispensing means to a shorter duration than desired. The dispensing apparatus may be a stand alone unit, or may be incorporated into a domestic or commercial air-conditioning or air-circulation unit for example.

The sink may be provided in the base of a dispenser, as a cavity that may be enclosed and may be sealed with a cover that has a small opening to receive the drain in the form, for example, of a 3 mm porous rod. The cavity can act as a sink and it may be filled with a porous granular material, crystals, cellulosic, or porous plastic which will receive excess material from the drain. In embodiments, the top of the screen is supplied with fragrance from the wick through making contact with a deformable pad. This may be squeezable to absorb fragrance that can used to prime the top of the screen so it can be established more quickly than by capillary action alone. A seal is removed from the surface of the pad so that the unit can be activated.

The sink may collect the residues carried by the less volatile components of the material. This allows the sheet to be substantially free of residues thus providing a linear weight-loss performance of the fragrance over the lifetime of the product. The reservoir houses the constant level means described in U.S. Pat. No. 7,360,671 which may be a tube enclosing the supply wick. When the reservoir is exhausted the sink may have absorbed the washed down residues including lower volatile components of the liquid. Replacing the fragrance reservoir module may allow the unit to continue operating at maximum efficiency. The perforated dispersal screen would not under normal circumstances require replacing due to the siphon-driven constant irrigation of the system. The sink and reservoir may be formed as a single unit, which can be replaced in one action.

In alternative embodiments, a sink may not be provided, for example where no residue from the carrier material or material to be dispensed reaches the base of the screen before evaporating. In this case, the base of the reservoir which holds the carrier material may be arranged with its base close to the base of the dispenser.

The base of the dispenser may wholly or partly correspond to the reservoir. In this way, the material to be dispensed can be stored as low as possible. This creates a stable dispensing device with a lower centre of gravity.

The reservoir formed in this way may be replaceable. The reservoir formed in this way may be made from a transparent material such as UV screened plastic.

This will allow a user to determine when the material to be dispensed has been used up.

Preferably, the volume of the reservoir is greater than the volume of material to be dispensed supplied with the reservoir. In this way, if the device is tipped over on its side, the resulting liquid level may be below a level at which it can run out of the reservoir. For example it may be below the level of a device for feeding the material to be dispensed such as a wick when the device is tipped over.

The sheet or sheets of embodiments of the invention may be used as the dispensing means in a dispenser according to the second aspect.

DETAILED DESCRIPTION OF EMBODIMENTS OF THE INVENTION

Detailed embodiments of the invention will now be described, purely by way of example, with reference to the accompanying drawings, in which:

FIG. 1 shows a sheet of material for dispensing, by evaporation, a volatile material, according to a first embodiment of the invention;

FIG. 2*a* shows a sheet of material according to a modification of the first embodiment of the invention;

FIG. 2*b* shows a sheet of material according to a further modification of the first embodiment of the invention;

Figure 1:
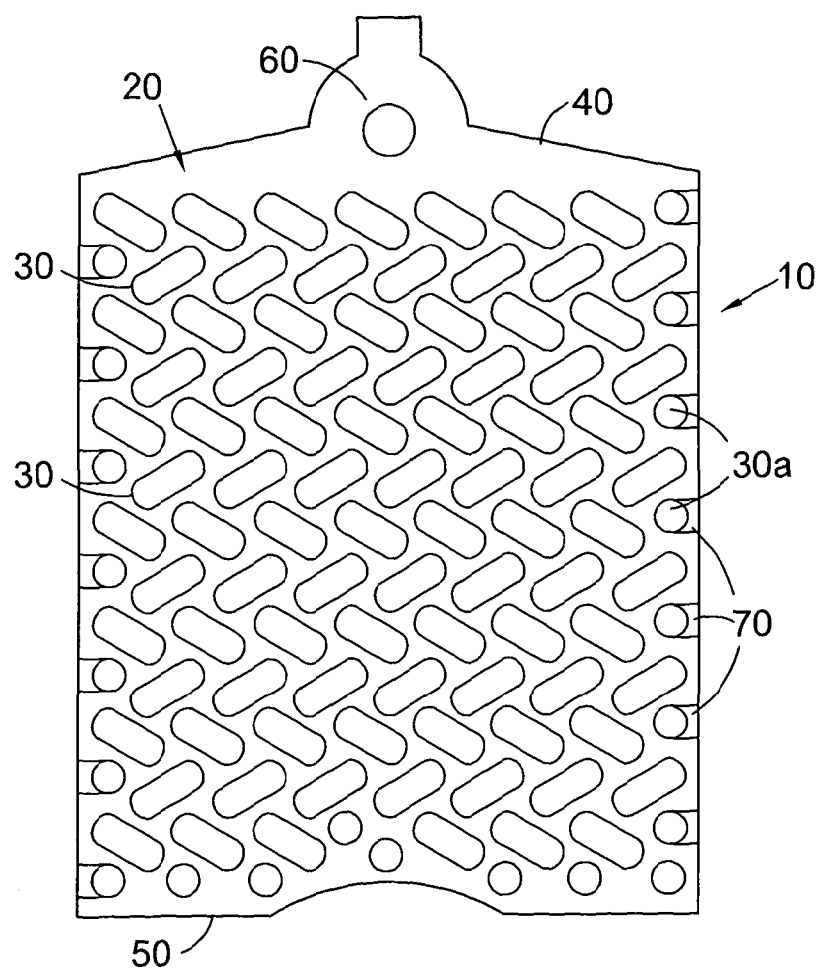

FIG. 1 shows a dispensing screen 10 according to a first embodiment of the invention, for dispensing, by evaporation, volatile materials applied thereto, which comprises a substantially flat sheet 20 of material, and diverting means 30 formed in the plane of the sheet 20, wherein the diverting means 30 form a minimum path length in the plane of the sheet 20 between at least a portion of a first edge 40 and an opposing second edge 50 of the sheet, which minimum path length is longer than the distance between the first and second edges 40, 50.

In the present embodiment, the diverting means 30 are formed as elongated holes 30 with rounded, or semicircular ends, the elongated direction of which are set at an angle to the width of the sheet 20. Adjacent rows of holes 30 are angled in the alternate sense from the first edge 40 to the second edge 50 to form a herring bone pattern. The adjacent holes 30 overlap in the direction from the first edge to the second edge, so that no straight line of material is formed between the first 40 and second 50 edges. In this way, the path length of volatile material and carrier travelling from the first edge 40 to the second 50 edge must be greater than the distance between the first 40 and second 50 edges.

In use, the sheet is mounted vertically with the first edge 40 substantially vertically above the second edge 50. On the first edge 40 is provided a receiving area 60 for receiving volatile material and carrier material thereon. In order to prevent the volatile material from travelling straight down the side edges and thereby not following a convoluted path, impermeable material 70 is placed on the sheet 20 from edge holes 30a, which are circular rather than elongated due to their positioning on the sheet 20. In this way, as the volatile material cannot travel through the impermeable material, it is forced to travel around the circular holes 30a when travelling from the first edge 40 to the second edge 50. The other feature involves impregnating the surface of the sheet at various points to prevent the liquid from having a direct route vertically down each side of the sheet. The impermeable material 70 impregnated in the sheet 20 also provides mechanical support to the sheet 20.

The sheet in the present embodiment is formed of paper. In the present embodiment, the paper reference is 1783/1 Hollingsworth & Vose. The paper is 0.4 mm thick. A thin material is used to reduce the volume of the fragrance loaded on the sheet 20 so that it maximises the surface area to volume of the liquid contained inside the fibrous paper material. Another reason for using a thin material is when the dispensing system is first activated (by connecting the fragrance to the top of the sheet), the system obviously will load quicker by requiring less liquid to be absorbed by the sheet. As the fragrance loads onto the sheet fragrance is released. Instead of paper, a porous plastic could also be used.

The 'herring bone' design is not used only for aesthetic reasons, but a purpose is to slow the rate of flow of a volatile liquid down the sheet so that there is sufficient time for most of the fragrance material to evaporate from its surface. The pattern can achieve this slowing effect in two entirely different ways.

Firstly, the convoluted path taken by the liquid in this embodiment is over 1.75 times further than the vertical path from top to bottom of the sheet 20. This is due to the holes 30 removed from its surface in the form of a herring bone pattern. Having further to travel the liquid has more time to evaporate for a given rate of flow.

Secondly, the structure of the paper sheet 20 around the holes 30 provides the only path for the liquid to travel. This path is convoluted by the alternating holes which are at least 60 degrees to the vertical. The forces acting upon the liquid molecules singularly and collectively are capillary action and gravity. Capillary action is the main force when initial charging of the fluid circuit takes place. Once the sheet 20 is charged with the material, then gravity becomes the strongest influence. The convoluted path of the sheet 20 weakens the effect of gravity upon the liquid, so that the flow rate is much slower than it would be if it were travelling vertically.

The longer path length and the weakening of the effect of gravity work in combination together. This provides more time to evaporate most of the product, but still allows the lower volatility components (so-called "bottom notes" of the fragrance) passage to the sink to irrigate the substrates, preventing a build-up of sticky residues in the fibres of the sheet.

Figure 2A:
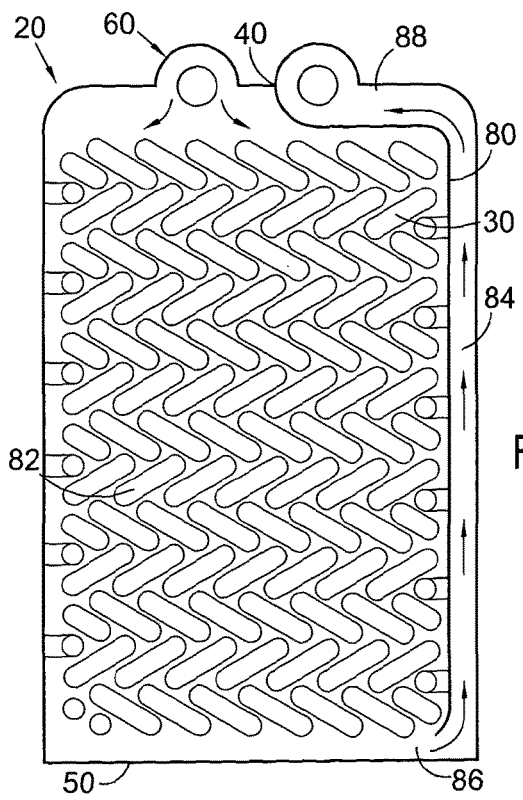

FIG. 2a shows a variation of the first embodiment, which is similar to that shown in FIG. 1, so that only differences in this variant will be described herein. In this variant, the sheet 20 is divided into two regions 82, 84 by an impermeable element 80 extending from the first edge 40 towards the second edge 50 to divide the first edge and at least part of the sheet 20 into two portions, a first region 82 of the sheet comprising the diverting means (in the form of elongated holes 30) and a second region 84 providing a direct communication channel from a communicating region 86 near the second edge 50 to the second region 88 of the first edge 40 to allow material that has reached the second edge to return to the second region of the first edge.

The connection points at the top of the sheet are marked in the figure with arrows that indicate the direction of the flow of the liquid. It can be seen that the main body is supplied with liquid from one of the connection points 60 for it to flow down the sheet 20. Conversely the other connection point 88 receives liquid (via the channel), from bottom of sheet 20.

It can be seen that several sheets may be connected in series. By providing a further similar sheet 20 rotated 180° through its vertical axis, the sheets may be connected together in series in a way that ensures that the flow of liquid always passes downwards any number in the series of sheets. This feature made possible through the permeability of the emanating system—provided by the holes 30—can produce a higher output for a given volume/space/height of dispenser, and allows for a compact design. Annular spacers (not shown) are placed between the adjacent sheets 20 to keep them a small distance apart from each other. The spacers may be of two types of materials: absorbent and non-absorbent. In this way, if so desired several sheets may be connected in a stack. The first sheet is placed adjacent to an absorbent component that may have a fixed position on the manifold so that is can receive a supply of product from a pad being pushed down upon it. The other sheet or sheets may be assembled using the appropriate type of spacer in between. Alternatively, the supply of the liquid product may be connected to the first sheet through a manifold comprising of two cylindrical bars perpendicular to the screens. A reservoir/wick supplies fragrance to a pad inside the top of the outer enclosure that pushes down to make contact with the manifold.

The height of the emanating sheets 20 may be varied in accordance with the angles of the holes 30 in the surface and the volatility of the material to be dispensed. Increasing the height of the screen increases the height of the column of liquid being supported by the emanating sheet. It is more efficient at emanating the product because of the 'thinning' out effect of the liquid due to the pull of gravity acting on a longer column of liquid increasing the surface area of evaporation.

The impermeable elements may extend all around at least the side the edges of the sheet to give support to the absorbent paper sheet.

Figure 2B:
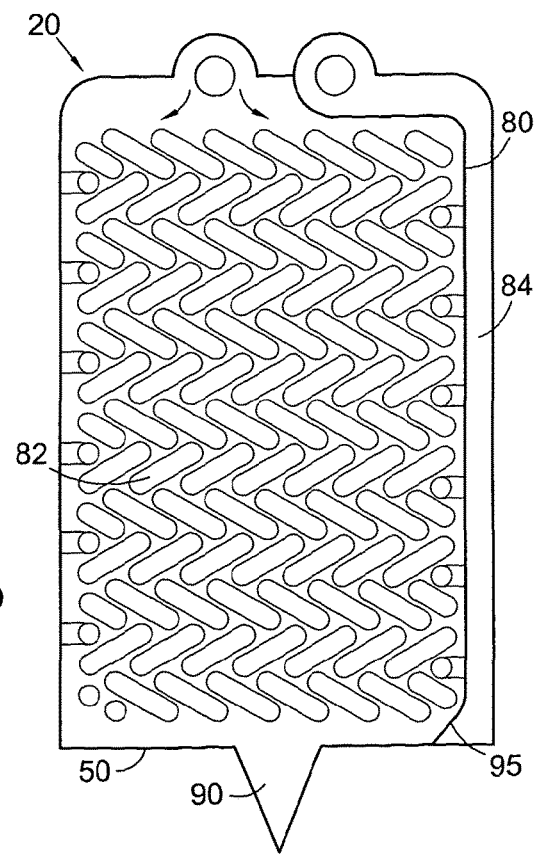

FIG. 2b shows a further variant of FIG. 2a, which is the same as FIG. 2a with the exception that an extending portion 90 is provided on the second edge which allows volatile material and carrier material that has reached the second edge 50 of the sheet 20 to drip down from the sheet 20, for example into a receptacle, such as a sink as described below. Further, in this embodiment, the communicating region between the first and second regions 82, 84 near the second edge has been closed off to prevent material from returning to the top of the sheet 20 via the second portion. Alternatively, the second portion 84 and the impermeable element 80 may be omitted completely in this variant. If a number of sheets are joined together in series the final sheet has a drain at the bottom which is hydrostatically the lowest point in the system. This enters a cavity completely free from any contact so that it can drip the excess liquid into the sink containing highly absorbent granules or porous plastic.

Figure 3:
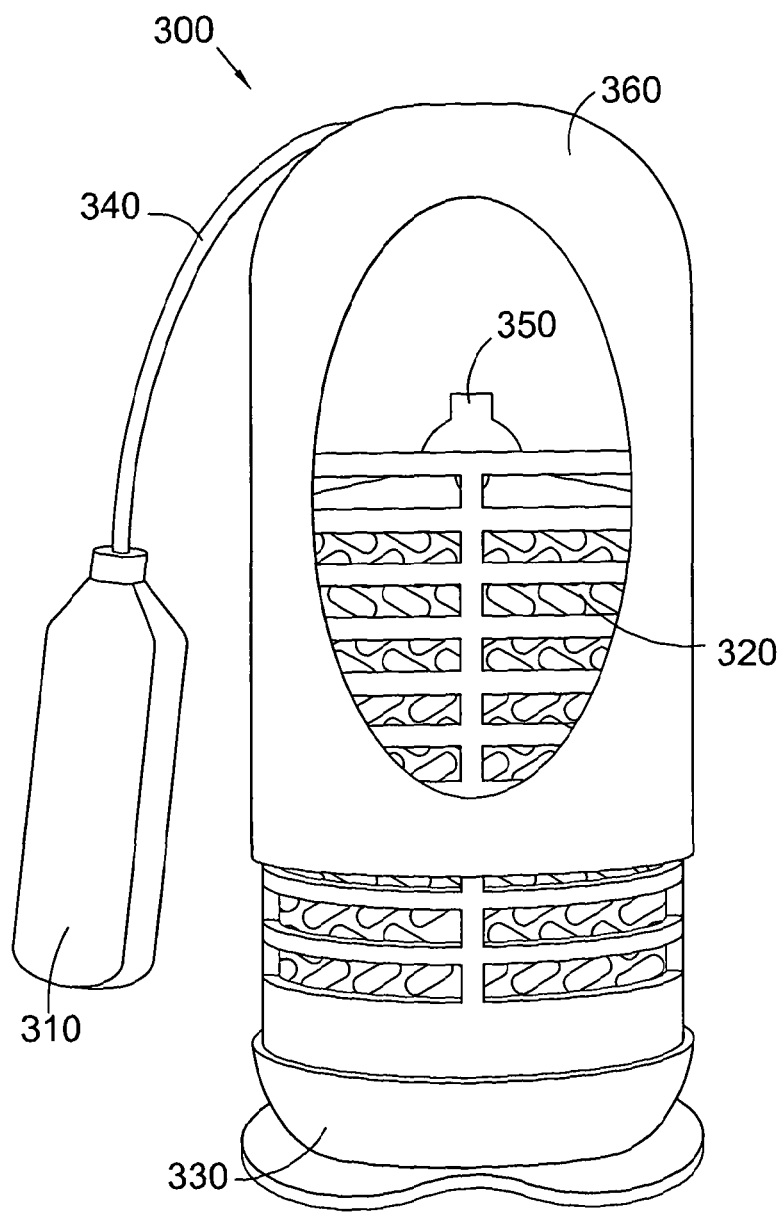
FIG. 3 shows a dispenser incorporating a sheet of material according to the first embodiment.

FIG. 3 shows a dispensing apparatus 300 for dispensing volatile materials by evaporation according to an embodiment of the invention. The apparatus 300 comprises a reservoir 310 for material to be dispensed, dispensing means 320 configured to allow evaporation of material from the reservoir to be dispensed; and a sink 330, in use below the dispensing means 320, configured to receive and retain material from the dispensing means 320 which has not evaporated from the dispensing means 320.

The sink 330 is an enclosed space filled, in the present embodiment, with ABSODAN PLUS Multi-purpose absorbent granules type 111/1 (111/R) the granules are about 1 mm in diameter and they are extremely efficient absorber of oils. However, other absorbent materials could be used, such as porous plastic, as appropriate.

The reservoir 310 is joined to the dispensing means 320 by a wick 340 and a connector 350 which the wick 340 engages when a cover 360 is closed, which activates the product by allowing the wick 340 into communication with the connector 350 and thereby to the dispensing means 320, which in the present invention is a screen comprising a sheet according to the first embodiment. In the present embodiment, the wick feeds the sheet by siphonic action. However, in alternate embodiment, where a liquid has a high volatility and a low viscosity is used, siphonic action may not be used. An example is the liquid EXXSOL D 40, ISOPAR-L and ISOPAR-M which is used as a carrier for an ingredient to kill mosquitos.

The capillary system linking the supply to the sheet would be the same but in this case, a sink is not required. There is a point on the sheet where, "the rate of propagation" is equal to "the rate of evaporation" (at a given temperature), and there is not any presence of volatile material below that point. The reservoir supply from the constant level in such an embodiment is positioned lower than the level at that point of equilibrium on the dispensing sheet to create a negative hydrostatic head to provide control and variable adjustment. The system is not then driven by a siphon but by capillary action plus evaporation.

In the present embodiment, the system in this case operates as a siphon, and is required to be highly positively biased in order to drive the liquid down the emanating screen.

Figure 4:
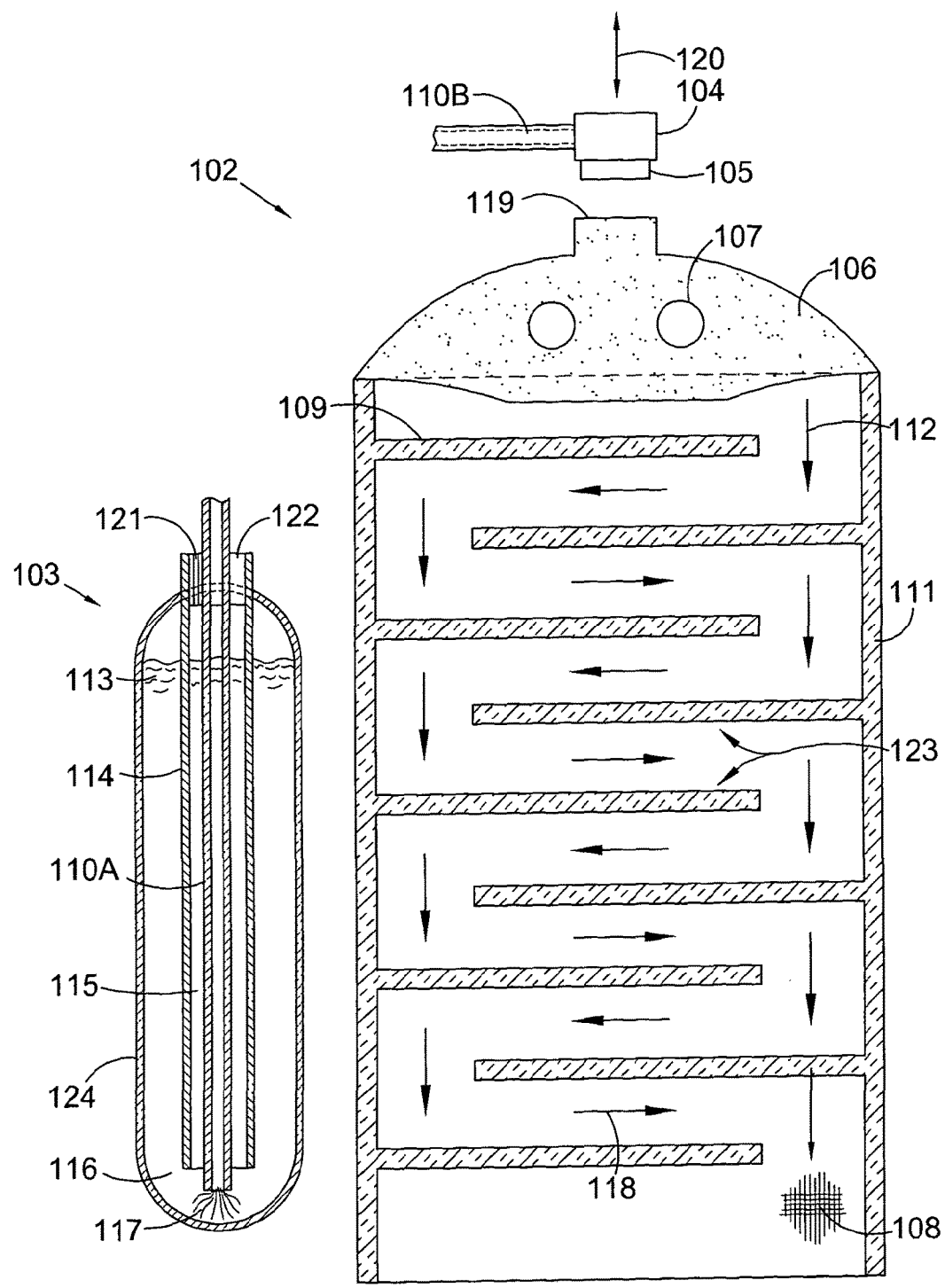
FIG. 4 shows a sheet according to a second embodiment of the invention.

FIG. 4 shows a dispensing screen according to a second embodiment of the invention. In this embodiment, the sheet is designed primarily for use with insecticides, rather than fragrances to be dispensed.

The figure shows a dispensing assembly 102, comprising a sheet of material, and a hydrostatic pressure compensated reservoir 103.

The pressure compensated reservoir 103 is of the type shown in U.S. Pat. Nos. 6,631,891 and 7,360,671 for providing a reservoir that can supply a liquid product from a constant level that is maintained at atmospheric pressure. It is used in the same manner as disclosed in these documents to provide the volatile material to the top of the sheet.

The formulation for the liquid 103 to be evaporated by this dispensing system uses a highly volatile low viscosity carrier material that contains an active ingredient. The high volatility and low viscosity of the liquid cause it to travel relatively quickly over an area of the sheet by capillary action, without assistance from gravity. Further, because of its high volatility, its rate of evaporation may be uncontrollably high, particularly at higher temperatures. To counter this, it can be seen that the fabric sheet 108 has been provided with a series of alternating diverting means in the form of impermeable regions, more particularly, horizontal impermeable "walls" 109 that define pathways 118 that greatly limit the effect of gravity acting on the liquid. The total length of the alternating pathway indicated by the arrows 112/118 is many times greater than the vertical length of the sheet 108. This arrangement makes the dominant force—capillary action because the horizontal walls support a substantial amount of the liquid against the force of gravity. Also, the distance between the impermeable walls 109 provides a narrow passage 123 that is uniform, from the top to bottom of the sheet.

The pathway 118/123 is a uniformly defined channel that alternates from left to right down the sheet from the first edge at which the volatile material is added to the second, opposite, edge. The liquid product is never likely to reach the bottom of the sheet in the present embodiment, due to its volatility, and the normal range of ambient temperatures. The distance travelled by the liquid 113 may be defined by the ambient temperature and hydrostatic forces produced by the arrangement of the system. The liquid 113 will travel to a point along the pathway where the "rate of propagation equals the rate of evaporation". At this point onwards, there is no presence of liquid. At higher ambient temperatures the liquid travels shorter distances along the prescribed pathway. To summarise the effects, at lower ambient temperatures the liquid product is evaporated from a larger area of the emanating surface as the volatility is lower and the product can reach further along the product before it evaporates. At higher ambient temperatures the liquid product is evaporated from a smaller area of emanating surface. Therefore, output (weight-loss) is controlled by this intrinsic temperature compensating characteristic of the delivery system and that the output is roughly the same for a range of temperatures.

Figure 5:
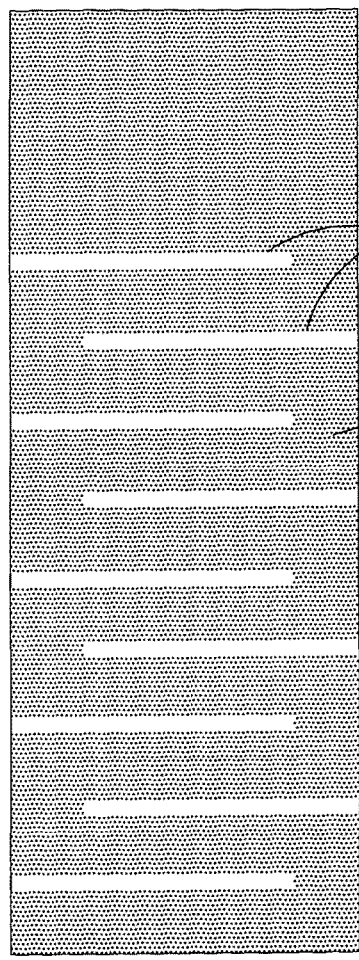
FIG. 5 shows a sheet of material according to the second embodiment of the invention.

As shown in FIG. 5, the walls 109 in the fabric sheet 108 may be created by impregnation of a suitable material to provide a barrier to the liquid product or alternatively, by a laser means that welds the fibres together at the appropriate places. The vertical walls 111 are not essential for the system to function but add mechanical support of the fabric. The woven polyester fabric screen is a very light material. It is approximately 0.28 mm thick and a sheet of length 120 mm; width 60 mm weighs only about 0.75 g. Its lightness means that the loading of the liquid product onto the screen is relatively low. The material has a relatively high void ratio that provides it with a high evaporative capacity. Note that there are three 'warp' fibre structures equidistantly spaced between any pair of the walls in the present embodiment, although this could be altered as required. These structures are bunches of fibres that are responsible for carrying the liquid 113 horizontally from side to side of the sheet of material. The fine 'weft' structures provide the vertical downward paths connecting everything together from top to bottom. A white liquid gel pen was successfully used to produce the walls in the present embodiment, although other suitable materials could also be used, in addition to melting of the fibres together to form a solid wall of material through which the volatile material cannot pass.

The top of the fabric sheet is attached to a porous plastic support 106 by stitching or crimping. Gluing between the fabric and the porous plastic may act as a barrier preventing the flow of liquid, so it is avoided in the present embodiment. However, were there no such barrier to the flow of the liquid formed, then gluing could also be used. The two holes 107 are to support the fabric sheet at the top so that the sheet hangs vertically downwards within a vented enclosure (not shown). The top of the porous sheet presents a surface 119 uppermost for making a connection with an absorbent contact pad 105 which is enclosed by a holder 104. The contact pad 105 is in intimate contact with one end of a wick 110B.

The contact pad 105 can be part of a vented enclosure that can be pushed down around the sheet so that there is a contact pressure between the pad 105 and the surface 119 at the top of the sheet 102. Alternatively, there may be a means 120 where a threaded component may cause the pad 105, by a means of rotation, to be brought into contact with the uppermost surface 119 of the sheet. This is a simple means for switching the dispenser "on or off". The wick 110A-110B connects the reservoir to the contact pad at the top of the dispenser. The wick is enclosed inside a flexible tube so that there is no loss by evaporation prior to the liquid arriving at the sheet 102.

In other embodiments, the reservoir 103 would have a rigid outer body 124 that is transparent so that the user would be able to determine when the reservoir 103 was exhausted and needed replacing. However, in the present embodiment, the active ingredient in the formulation deteriorates in the presence of daylight over time, so light has to be prevented from entering through the reservoir wall 124 and also the flexible tube enclosing the wick. There is fresh liquid coming down from the top of the sheet all the time that the system is switched on. The delivery system is complimentary to the active ingredient by continuously refreshing and replacing the liquid over the emanating surface limiting the amount of time that the active ingredient is exposed to daylight.

Experiments were carried out with the liquid carrier EXXSOL D40, ISOPAR-L and ISOPAR-M without the active ingredient. In the present embodiments the active ingredient is in a low concentration approx 0.2%. Other possible carriers could be used subject to testing of volatility and performance. These are: EXXSOL D80 and EXXSOL D100.

Figure 6:
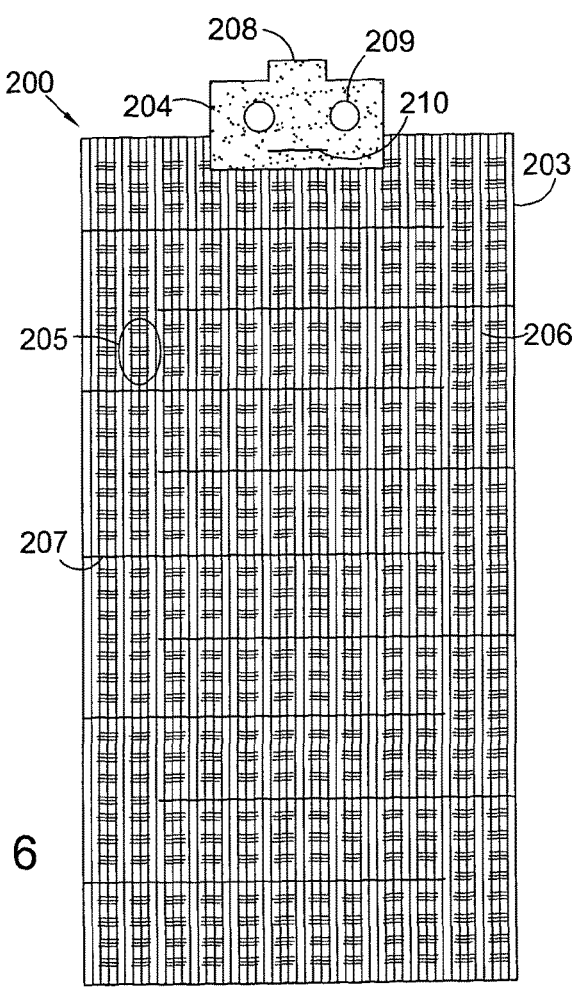
FIG. 6 shows a variant of the second embodiment of the invention.
Figure 7:
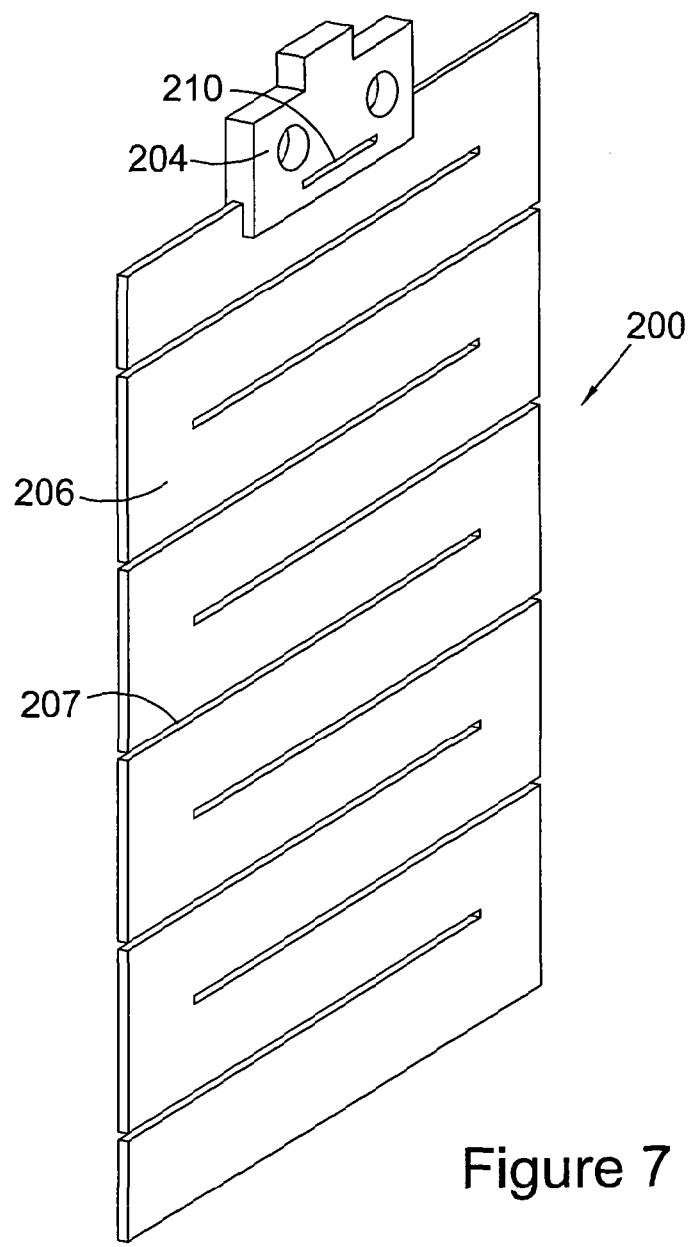
FIG. 7 shows a perspective view of the variant of FIG. 6.

FIG. 6 shows a further variation of the screen according to the second embodiment of the invention. The drawing shows the dispensing assembly 202 comprising two main parts. In many respects it is similar to that described above, so only differences will be described below.

The main body of the sheet is made from a woven polyester fibrous fabric material 203 which is supported at the top by a porous material 204.

The porous material 204 may be slotted so that it can pass over the upper edge of the woven material and then secured together by a staple or crimp means 210. Alternatively the porous material may be stamped out and folded at region 208 so that the two sides go either side of the fabric and then stapled at 210.

The porous material provides a means of support for the downwardly extending fabric material while also providing a connection between the capillaries of the porous support 204 and the capillaries of the fabric sheet.

The holes 209 of the porous support 204 provide a means of anchoring the assembly to the upper part of a dispensing means enclosure (not shown), so that the fabric sheet 203 can hang within an enclosure that allows air to go through from either side of the fabric.

The upper portion 208 of the porous support 204 provides a means of contact with a pad (not shown) that can be brought into contact with it. The pad is supplied with liquid product from a wick that is connected to a hydrostatically pressure compensated reservoir. This means that the dispensing means may be switched on or off.

The fabric sheet 203 is aligned so that the 'weft' structures 206 are vertically disposed and the 'warp' structures 205 are horizontally disposed. The 'warp' structures 205 contain more fibres in a group than the weft structures 206 of the fabric and so have a larger capacity for carrying liquid product (not shown). Regions 207 that are impermeable to the liquid product are created in the fabric by a means of heat fusing the fibres along the 'warp' structures using an automated laser means. The walls 207 alternate, left to right and right to left.

They are regularly spaced and terminate short of the opposite end so that a gap is provided at the end of each wall to allow the liquid to travel down the 'weft' structures to the next space between the subsequent pair of walls. This extends the path length by several times and inhibits the effect of gravity acting on the liquid product.

It can be seen that the spacing between the walls 207 provides a consistent uniform pathway for the liquid product comprising mainly of three 'warp' structures 205 positioned equidistantly between any pair of horizontal walls 207. Therefore the load carrying capacity of each pathway for the liquid product is the same. As has been mentioned the liquid product is highly volatile and that is the reason that the fabric pathway has been designed in this way by maximising the use of capillary forces. However, hydrostatic forces can have a big part to play in association with the capillary forces by providing a variable output up to four times the lowest amount (the amount of product evaporated over a period of time).

This is achieved by making the reservoir able to slide up or down in the vertical plane. This of course uses the benefits of the pressure compensated reservoir in maintaining a constant level irrespective of the height of the liquid product in the reservoir. Raising the reservoir increases the output and vice versa, lowering the reservoir lowers the output. Also the constant level ensures that the output is substantially linear over time.

As discussed above, how far the liquid travels around the fabric circuit depends upon the temperature. As the temperature increases, there is an increase in the volatility of the liquid product and therefore the liquid evaporates at a faster rate and will only travel a relatively short distance along the pathway. When the temperature is lower, the volatility of the liquid is reduced and evaporated at a lower rate. Therefore the liquid, on average, travels to a point further along the pathway before evaporating. The temperature compensation effect can be seen as the result of a higher volatility of product dispensed from a smaller surface area equates to a lower volatility of product evaporated over a larger surface area.

The dispensing means for the volatile insecticide product in this embodiment does not require a sink because there are no residues to collect. There are just two main components, the PCR and the dispensing assembly together forming a very simple construction.

The fabric is highly permeable due to having a high void ratio in its structure. It has a very low mass 0.75 g and is 0.34 mm thick and because of this it has a very low take-up volume of product. It should be enclosed inside a holder that is highly perforated so that the liquid product is free to evaporate in to the air.

Benefits of a dispenser according to the second embodiment of the invention include substantially constant output of product over time from start to finish of the life of the product. Further, the replaceable reservoir cartridge when the reservoir becomes exhausted means that it can be reused. The device is switchable when not in use—as it may be switched off when not in use, the use of the product can be prolonged, and the product can be transported and stored after initial use has begun. In other embodiments, however, the switch may be omitted. The output may be adjusted to the volume of space to be safeguarded.

As described above, the system provides stable performance over varying temperatures. Even though the active ingredient may be adversely affected by light over time, the system provides very low loading of product on the dispensing screen; its rate of evaporation is relatively high and the exposure is short.

Figure 8:
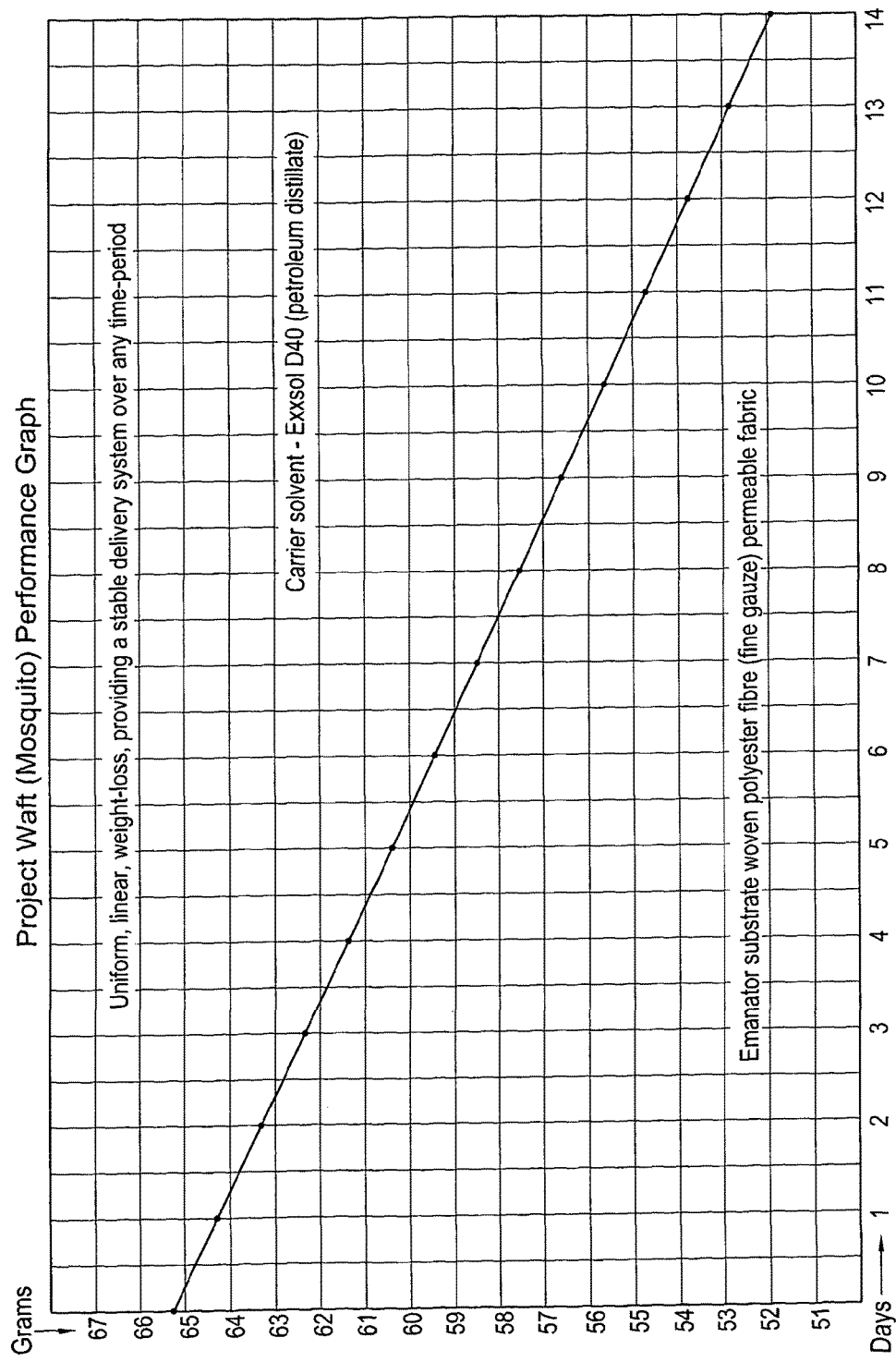
FIG. 8 is a graph showing the constant rate of evaporation of volatile material from a sheet according to the second embodiment in a dispenser.

FIG. 8 shows the high linearity of weight loss in the reservoir of the second embodiment of the invention over time, in use and, therefore, the consistent dispensing by evaporation of the volatile liquid. Table 1 shows the experimental results of evaporation amount over a period of time of a dispenser according to the second embodiment in use.

A further embodiment of the invention will now be described with reference to FIGS. 9 and 10. The figures show an alternative embodiment, which is similar to the embodiment shown in FIG. 3 and described with reference thereto. A reservoir 910 is provided, which includes the volatile material. Inside the reservoir 910 is provided a wick 940 which extends from close to the bottom of the reservoir 910, when it is in an in use configuration, through the top of the reservoir 910 and is sealed with a plug 915 to, which seals the top of the wick 940 before the reservoir 910 is installed in the dispensing unit 900. The wick 940 is surrounded by a cylindrical covering 914, which allows volatile material to enter the wick 940 only at its top and bottom ends. The wick 940 is inserted into the reservoir 910 within a surround 916 which extends around the elongated axis of the wick 940 within the reservoir 910. The surround 916 comprises an air channel 917, which extends from an interior to an exterior side of the reservoir 910. A cap 918 is provided on the interior end of the surround 916. The cap 918 is pushed off the end of the surround 916 as the wick 940 is pushed into the reservoir 910 from a storage position to an active position, as shown in the figure. As the cap 918 is removed from the end of the surround 916, the volatile material forms an interface with the column of air inside the surround 916, which forms a constant level, whilst the end of the wick 940 enters just below the surface of the liquid that forms an interface with the column of air. The air channel 917 is thus in communication with the inside of the reservoir 910.

Surrounding the reservoir 910 is the screen 920. The screen 920 is formed of a sexangular mesh fabric. In the present embodiment, the screen (920) is a vertically arranged generally cylindrically extending member with its cylindrical axis substantially parallel to the cylindrical axis of the wick 940. The screen 920 is secured at the top of the unit 900 to an upper support 960, which extends substantially horizontally. In the centre of the upper support 960 a connector 950 extends therethrough, which contacts the top of the wick 940. The connector 950 is porous and allows volatile material exiting the reservoir 910 via the wick 940 to flow to a disk 965 mounted above the upper support 960 which allows communication of the volatile material from the wick 940, via the porous connector 950, and the disk 965 to the top of the screen 920. In the present embodiment, the disk 965 is formed from paper, although other materials which will conduct the volatile material from the wick 940 to the screen 920 could also be employed. An annular porous washer 967 is also provided around the porous connector 950 to aid the flow of volatile material from the wick 940 to the screen 920. The washer 967, disk 965 and upper support 960 are clamped together by clamp means 979, which also secures the porous connector 950 in position. The screen 920 is clamped at its lower end to a lower support 970. The upper and lower supports 960, 970 are connected and maintained in constant separation by substantially vertical supports 975. In the present embodiment three supports are provided, although any other suitable number could also be used. The lower support 970 includes an annular duct 974, below an annular sealing ring 976, which clamps the screen 920 to the lower support 970 adjacent its lower end. The annular duct 974 is provided with a number of drain elements 978, which allow any excess volatile material that has reached the base of the screen 920 to be collected and to be discharged from the annular duct 974.

Below the reservoir 910 and lower support 970, there is provided a sink 930. The sink 930 has a central cylindrical central portion 932 which is raised. This portion engages with a correspondingly dimensioned extending portion of the lower support 970 so that the lower support 970 is retained and supported by the sink 930. The sink 930 comprises a housing 934, on which the raised portion 932 is formed. Inside the housing 934 there is provided porous plastic 936, which absorbs excess material dripping from the drain elements 978 into the sink 930 via correspondingly placed holes in the housing 934. The porous plastic 936 absorbs any excess volatile material that reaches the lower end of the screen 920 as described above. The operation of the unit in terms of evaporation of the volatile material is as described in previous embodiments. In an alternative embodiment, the sink 930 is formed of a single block of porous plastic 936, enclosed inside the casing. When the unit is activated, the upper and lower supports 960, 970 together with the porous elements clamped thereto are placed over the reservoir 910 which is retained on the sink 930. As the elements are pushed downwards onto the sink 930 over the reservoir 910, the lower support 970 engages with the raised portion 932 of the housing 934 of the sink 930. At the same time, the upper support 960, and, in particular the porous connector 950, is pushed down onto the contact pad 912, which, in turn, pushes down the wick 940 into the reservoir 910, which pushes off the cap 918 from the surround 916. This allows the volatile material in the reservoir 910 to form an interface with the column of air inside the surround 916 and also into contact with the interior end of the wick 940. The volatile material then travels up the wick 940 and to the screen 920 via the porous connector 950, the annular washer 967 and the disk 965. The unit then operates in the same manner as discussed above.

Figure 9:
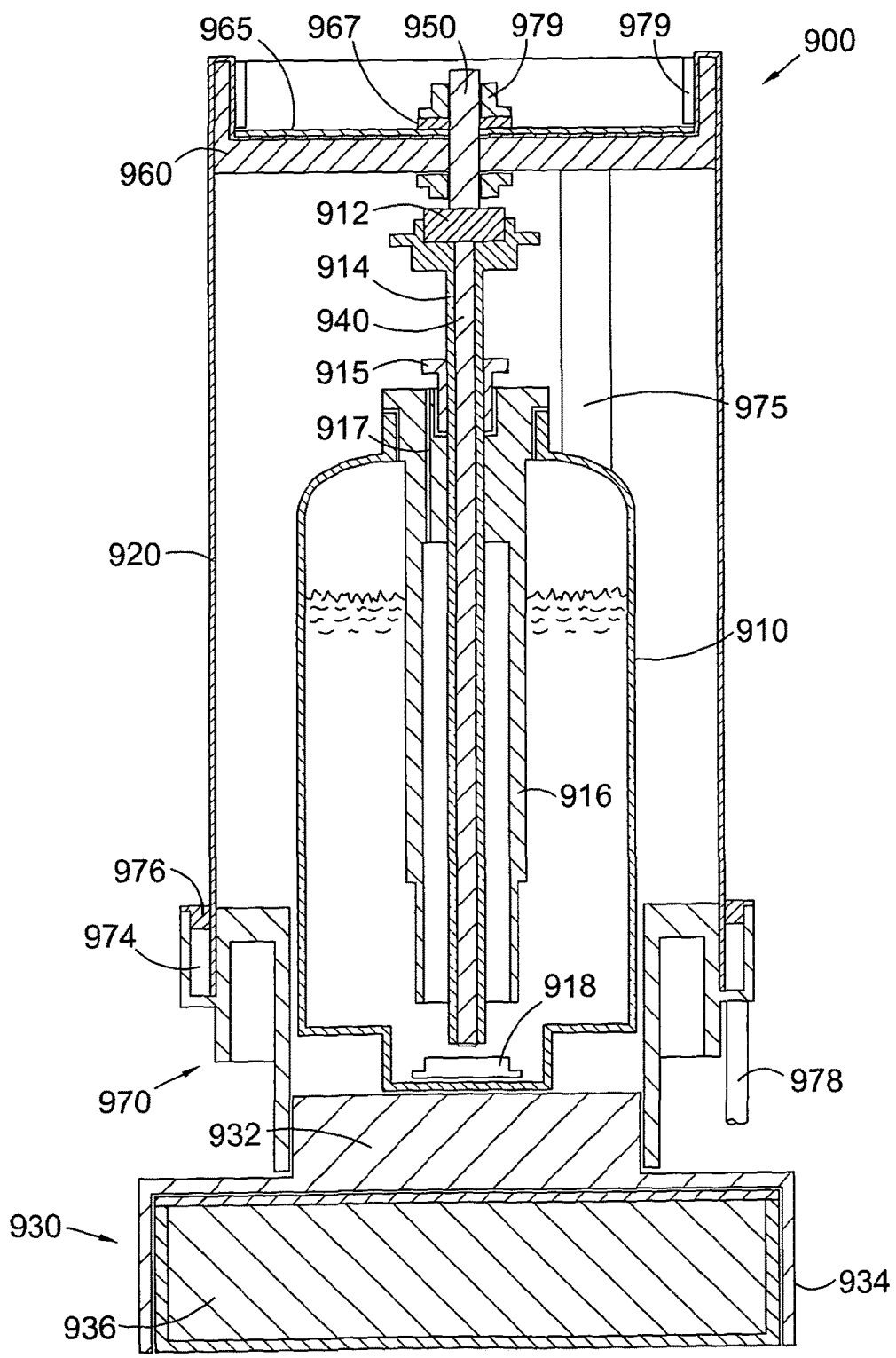
FIGS. 9 and 10 show a further embodiment of the invention.
Figure 10:
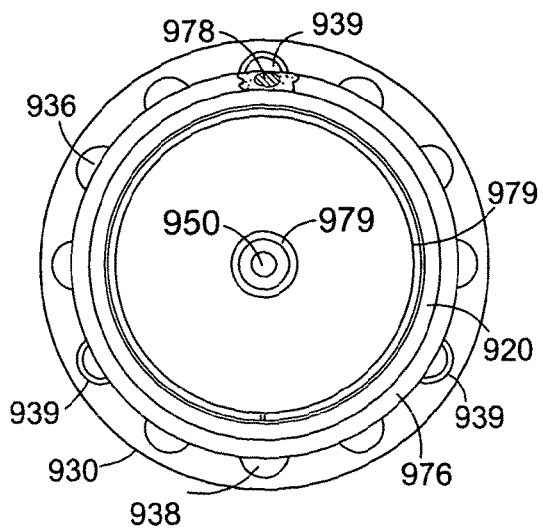

FIG. 10 shows a top view of the embodiment of FIG. 9. This view shows holes 938 in the surface of the sink 930 through which the porous plastic 936 can be seen. Three of these holes (numbered 939) are configured to align with the drain elements 978, the position of one of which is shown in a cut-away portion of the view.

Figure 11:
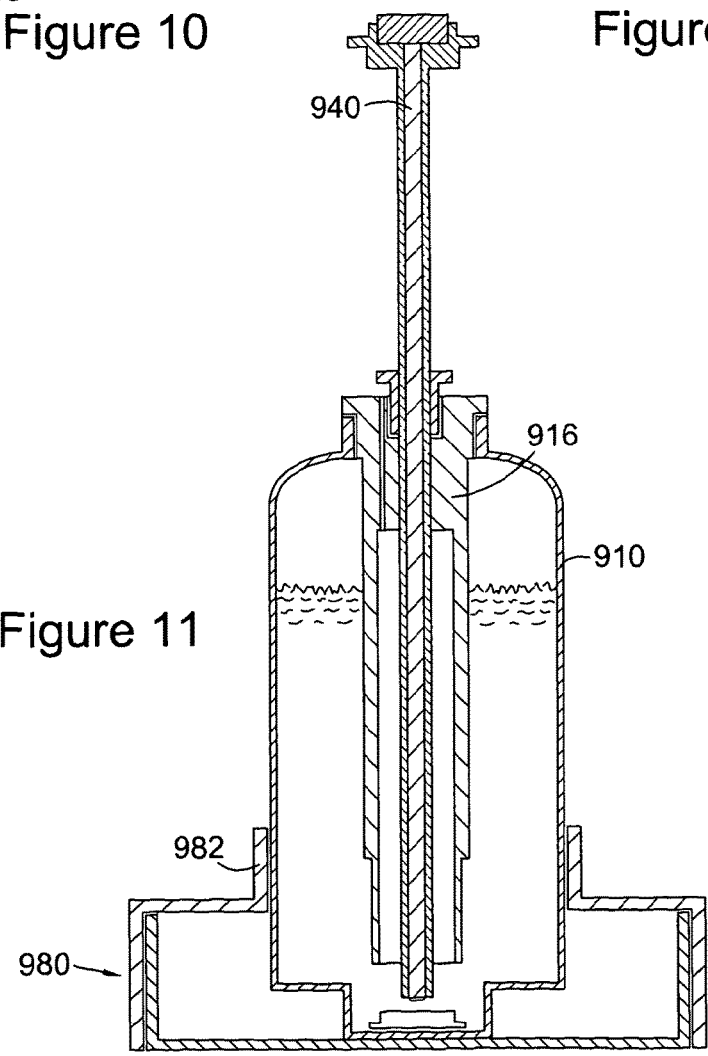

This embodiment is particularly suited to fragrances where a residue remains from the volatile material after it has passed all of the way down the screen 920. FIG. 11 described an alternative embodiment in which a sink 930 is not required, in the case where no volatile material remains at the base of the screen 920, adjacent the lower support 970, as all of the volatile material has evaporated before it falls to the lower part of the screen 920. The figure shows only differences between this embodiment and that described with reference to FIG. 9. Therefore, the screen 920, upper and lower supports 960, 970 and associated parts are not shown. The reservoir 910, wick 940 and wick surround are also the same as described in relation to FIG. 9 and will not be described further here. The difference is that a base 980 is formed. The base 980 has a cylindrical opening, which is dimensioned to correspond to the diameter of the reservoir 910. The reservoir 910 is then inserted into the opening until the bottom of the reservoir 910 is placed on an internal lower surface of the base 980 or forms the base of the dispensing apparatus. As no sink 930 is required in this embodiment, the lower support 970 (not shown) may be altered to remove the drainage elements and annular duct. The lower element surrounds and sits on an upper part of the base 980, and two vertical shoulders are formed around which the extending portions of the lower support 970 extend, for example in a friction fit.

Figure 12:
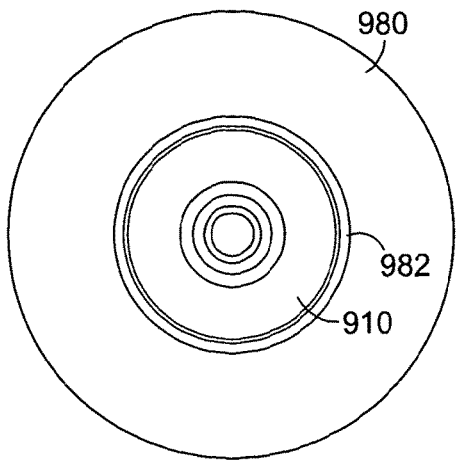
FIGS. 11 and 12 show a yet further embodiment of the invention.

FIG. 12 shows a top view of the embodiment of FIG. 11.

Once again, the operation of the unit is as described above.

There are several absorbent/porous components that connect together to form a capillary circuit that provides a conduit for the liquid product to be conducted from the reservoir 910 to the screen 920. They are connected in series starting from wick 940, contact pad 912, connector 950, porous washer 967, disk 965 and screen 920.

In the case of the fragrance delivery means (FIG. 9) the bottom of the screen 920 is extended by the three drain elements 978 so that it is hydrostatically biased to form a siphon to irrigate the screen 920 from the build-up of residues. This arrangement is hydrostatically biased to provide a force in the same direction as the flow from the reservoir to the screen. Therefore when the capillary circuit is fully charged the capillary force and the gravity force acting in the same direction support each other.

The hydrostatic bias is created by the bottom of the drain elements 978 being lower than the constant level means (surround) 916 (refer to FIG. 9. In this arrangement the liquid product is present in every part of the circuit formed by the interconnecting capillary components. At the end of the circuit are the drain elements 978 and these are in a fixed position. The reservoir 910 that includes the constant level means (surround) 916 can be moved vertically upwards relative to the fixed drain elements 978. This will increase the flow speed of the liquid product because of the increase in difference in height between the bottom of the constant level means 916 and the bottom of the drain elements 978. This allows fine tuning to optimise the performance so that the flow rate can be balanced to the evaporation rate of the product.

In the case of the insecticide delivery means of FIG. 11 it can be seen that the reservoir 910 is in a fixed position at the bottom of the assembly. There is no need for the drain elements 978 to remove residues because the formulation uses a solvent (ISO PAR-M) as a carrier for the active ingredient and they are both volatile. In this arrangement the bottom of the constant level means 916 is much lower than the bottom of the screen 920 which is attached to the support 970. This arrangement is not a siphon because it is hydrostatically negatively biased to the direction of the flow of liquid from the reservoir 910 to the screen 920 so that the capillary force and the gravity oppose each other. Because of the opposing forces the loading of the liquid on the screen 920 is less and the resulting high surface area to volume ratio creates a highly evaporative effect when used in conjunction with a polyester material for the screen 920 like the Litmans 573. This is a sexangular mesh fabric that is highly permeable and light-weight.

The rate of dispensing volatile material can also be adjusted by adjusting the tension applied to the material of the screen 920. In the embodiments described in FIGS. 9 and 10, the material is polyester. In the embodiment described in relation to FIGS. 11 and 12, the material is polyester 573 Litmans. In both embodiments described in FIGS. 9-10 and 11-12, it is important that the screen 920 is kept separated from the uprights as otherwise the volatile material can travel onto the uprights and travel directly downwards to the lower support 970, thus increasing the speed of dispensing of the volatile material. In alternative embodiments, the screen 920 may not be cylindrical but may be frusto-conical. The screen 920 is, in the present embodiment, made from two halves of flat material welded together at their lateral edges and bent into a generally cylindrical or frusto-conical form. The shape of the two halves of the screen 920 can be altered, in order to provide the described shape of three dimensional surfaces required. Additionally, it is possible to include an intermediate horizontal support part way between the upper and lower supports 970. Such an intermediate support would be attached to the upright support elements and support the screen 920 between the upper and lower supports 960, 970.

The present invention has been described purely by way of example, and various modifications, amendments, additions and omissions may be made, while falling within the scope and spirit of the invention. The terms "comprise", "comprising", "comprises" and the like, unless the context clearly implies otherwise, are to be understood in the inclusive, rather than exhaustive sense, i.e. "including but not limited to".

TABLE 1

| Date | time | weight | weight-loss |
| --- | --- | --- | --- |
| 27/07/10 | 10.30 am | 65.23 g | 0.99 g |
| 28/07/10 | 10.30 am | 64.24 g | 1.01 g |
| 29/07/10 | 10.30 am | 63.23 g | 0.96 g |
| 30/07/10 | 10.30 am | 62.27 g | 0.94 g |
| 31/07/10 | 10.30 am | 61.33 g | 0.98 g |
| 01/08/10 | 10.30 am | 60.35 g | 0.93 g |
| 02/08/10 | 10.30 am | 59.42 g | 0.94 g |
| 03/08/10 | 10.30 am | 58.48 g | 0.99 g |
| 04/08/10 | 10.30 am | 57.49 g | 0.91 g |
| 05/08/10 | 10.30 am | 56.58 g | 0.90 g |
| 06/08/10 | 10.30 am | 55.68 g | 0.93 g |
| 07/08/10 | 10.30 am | 54.75 g | 0.95 g |
| 08/08/10 | 10.30ann | 53.80 g | 0.92 g |
| 09/08/10 | 10.30 am | 52.88 g | 0.94 g |
| 10/08/10 | 10.30 am | 51.94 g | |

The invention claimed is:

1. A dispensing screen for dispensing, by evaporation, volatile materials applied thereto, the screen comprising: a sheet of permeable material defining a plane, a thickness, and having a first edge secured to a support of the dispensing screen and a second edge; and diverting means formed on or in the material of the sheet, wherein the diverting means comprises a plurality of holes formed in the sheet and each extending through the thickness and transverse to the plane, wherein the diverting means form a plurality of flow paths defined between the plurality of holes along the sheet each having a minimum path length, wherein the plurality of flow paths define all of the flow paths for volatile material flowing along the sheet between at least a portion of the first edge of the sheet and the second edge of the sheet, wherein the first and second edges of the sheet are opposite each other and the first edge is at a top of the sheet and the second edge is at a bottom of the sheet, with respect to gravity, wherein the minimum path length of each of the flow paths is longer than the distance between the first and second edges along the surface of the sheet, the minimum flow paths each being defined by a convoluted path in the direction from the first edge to the second edge.

2. A dispensing screen according to claim 1, wherein the sheet is formed from woven polyester fibre.

3. A dispensing screen according to claim 1, wherein, in use, volatile material applied to the first edge of the sheet travels towards the second edge at least partially by capillary action.

4. A dispensing screen according to claim 1, wherein, in use, volatile material applied to the first edge of the sheet travels towards the second edge at least partially under the effect of gravity.

5. A dispensing screen according to claim 1, wherein the sheet comprises joining edges which join the first and second edges, and wherein the diverting means further comprises impermeable regions extending from the joining edges to the holes closest to the joining edges.

6. A dispensing screen according to claim 5, wherein the impermeable regions provide structural support to the sheet.

7. A dispensing screen according to claim 1, wherein the plurality of holes are arranged in a herringbone pattern.

8. A dispensing screen according to claim 7, wherein the herringbone pattern is at least 60[deg.] to a line perpendicular to at least one of the first and second edges.

9. A dispensing screen according to claim 1, wherein the support includes a pad for receiving volatile material from a reservoir or wick connected thereto and supplying the material to the sheet.

10. A dispensing screen according to claim 1, wherein the sheet is wrapped into a cylinder or closed loop.

11. A dispensing screen according to claim 1, wherein the minimum path length of each of the flow paths is at least 1.75 times longer than the distance between the first and second edges.

12. A dispensing apparatus for dispensing volatile materials by evaporation, comprising: a reservoir for storing the volatile material before it is dispensed; a dispensing screen including: a sheet of permeable material defining a plane, a thickness, and having a first edge secured to a support of the dispensing screen and a second edge; and diverting means formed on or in the material of the sheet, wherein the diverting means comprises a plurality of holes formed in the sheet and each extending through the thickness and transverse to the plane, wherein the diverting means form a plurality of flow paths defined between the plurality of holes along the sheet each having a minimum path length, wherein the plurality of flow paths define all of the flow paths for volatile material flowing along the sheet between at least a portion of the first edge of the sheet and the second edge of the sheet, wherein the first and second edges of the sheet are opposite each other and the first edge is at a top of the sheet and the second edge is at a bottom of the sheet, with respect to gravity, wherein the minimum path length of each of the flow paths is longer than the distance between the first and second edges along the surface of the sheet, the minimum flow paths each being defined by a convoluted path in the direction from the first edge to the second edge.

13. A dispensing apparatus according to claim 12, wherein lateral edges of the screen, extending between the first and second edges, are joined to one another along at least a portion of their length.

14. A dispensing apparatus according to claim 12, wherein the dispensing screen is mounted around the reservoir.

15. A dispensing apparatus according to claim 12, further comprising a wick, extending from the reservoir to the dispensing screen and in fluid communication at or adjacent to the top of the dispensing screen to supply volatile material thereto.

16. A dispensing apparatus according to claim 12, further comprising a sink, in use below the dispensing screen, configured to receive and retain material from the dispensing screen which has not evaporated from the dispensing screen.

17. A dispensing apparatus according to claim 12, wherein the minimum path length of each of the flow paths is at least 1.75 times longer than the distance between the first and second edges.

18. A dispensing apparatus for dispensing volatile materials by evaporation, the apparatus comprising a reservoir for material to be dispensed; dispensing means configured to allow evaporation of material from the reservoir to be dispensed; and a sink, in use below the dispensing means, configured to receive and retain material from the dispensing means which has not evaporated from the dispensing means, wherein the dispensing means comprises a dispensing screen formed from a sheet of permeable material that defines a plane, a thickness, and includes a plurality of holes formed in the sheet of material and extending through the thickness and transverse to the plane, and wherein volatile material is applied to a first edge of the dispensing screen and travels to a second edge of the dispensing screen only along a plurality of flow paths defined between the plurality of holes and each having a convoluted minimum path length longer than the length between the first and second edges, wherein the first and second edges of the dispensing screen are opposite each other, and lateral edges of the screen, which extend between the first and second edges, are wrapped around and joined over at least a portion of their extent.

19. A dispensing apparatus according to claim 18, wherein the sink is not in contact with the dispensing means.

20. A dispensing apparatus according to claim 18, wherein a switch is provided to selectively allow volatile material to travel from the reservoir to the dispensing means.

21. A dispensing apparatus according to claim 18, wherein the sheet of material is mounted in an impermeable surround.

22. A dispensing apparatus according to claim 21, wherein the impermeable surround is connected to the dispensing means.

23. A dispensing apparatus according to claim 18, wherein the sheet of material is mounted around the reservoir.

24. A dispensing apparatus according to claim 18, wherein the sink comprises absorbent granules or porous plastic.

25. A dispensing apparatus according to claim 24, comprising a plurality of screens parallel to one another with their main sides facing one another.

26. A dispensing apparatus according to claim 25, comprising a spacer between each dispensing screen.

27. A dispensing apparatus according to claim 18, wherein the convoluted minimum path lengths are at least 1.75 times longer than the length between the first and second edges.

* * * * *